US009603637B2

(12) United States Patent
Northcutt et al.

(10) Patent No.: US 9,603,637 B2
(45) Date of Patent: Mar. 28, 2017

(54) POLYAXIAL INTERSPINOUS FUSION IMPLANT AND BONE GROWTH STIMULATION SYSTEM (71) Applicant: Aurora Spine, Inc., Carlsbad, CA (US)

(72) Inventors: Trent James Northcutt, Oceanside, CA (US); Laszlo Garamszegi, Mission Viejo, CA (US)

(73) Assignee: AURORA SPINE, INC., Carlsbad, CA (US)

( * ) Notice: Subject to any disclaimer, the term of this patent is extended or adjusted under 35 U.S.C. 154(b) by 32 days.

(21) Appl. No.: 14/732,240

(22) Filed: Jun. 5, 2015

(65) Prior Publication Data

US 2016/0015432 A1 Jan. 21, 2016

Related U.S. Application Data (60) Provisional application No. 62/009,129, filed on Jun. 6, 2014.

(51) Int. Cl.
 *A61B 17/70* (2006.01)
 *A61F 2/44* (2006.01)
(52) U.S. Cl.
 CPC ...... *A61B 17/7068* (2013.01); *A61B 17/7062* (2013.01); *A61F 2/44* (2013.01)
(58) Field of Classification Search
 CPC ............. A61B 17/7068; A61B 17/7062
 See application file for complete search history.

(56) References Cited

U.S. PATENT DOCUMENTS 8,236,031 B2 * 8/2012 Bucci ................. A61B 17/7062
 606/248
8,241,330 B2 * 8/2012 Lamborne .......... A61B 17/7068
 606/248

(Continued)

*Primary Examiner* — Ellen C Hammond
*Assistant Examiner* — Stuart S Bray
(74) *Attorney, Agent, or Firm* — Hybrid Law Group PC (57) ABSTRACT A polyaxial interspinous fusion device is described. The polyaxial interspinous fusion device has a fixed anchor, a polyaxial anchor, and a bone spacer. The fixed anchor has a center ring, one or more fixed anchor arms projecting laterally from the center ring, and a barrel projecting transversely from the center ring. The polyaxial anchor has a socket ring and one or more polyaxial anchor arms projecting laterally from the socket ring, wherein the socket ring has a concave engagement surface. The bone spacer has a spacer head having a convex socket engagement surface that matches the concave engagement surface of the socket ring. The bone spacer also has one or more zip lock flanges extending transversely from the spacer head and one or more bone abutments extending transversely from the spacer head. The zip lock flanges and bone abutments of the bone spacer fit through the socket ring and the barrel of the fixed anchor fits through the socket ring. The zip lock flanges engage with the barrel when the zip lock flanges and bone abutments are inserted through the socket ring. When the polyaxial anchor engages with the spacer head, the polyaxial anchor has a polyaxial freedom of movement relative to the spacer head as a result of a ball and socket engagement between the concave engagement surface of the socket ring and convex socket engagement surface of the spacer head.

7 Claims, 11 Drawing Sheets

(56) References Cited

U.S. PATENT DOCUMENTS

| | | | | |
|---|---|---|---|---|
| 8,262,697 B2* | 9/2012 | Kirschman | A61B 17/7058 | 606/248 |
| 8,343,190 B1* | 1/2013 | Mueller | A61B 17/7068 | 606/248 |
| 8,382,801 B2* | 2/2013 | Lamborne | A61B 17/7068 | 606/246 |
| 8,685,065 B1* | 4/2014 | Taber | A61B 17/7068 | 606/249 |
| 9,387,016 B2* | 7/2016 | Okamoto | A61B 17/7065 | |
| 2003/0040746 A1* | 2/2003 | Mitchell | A61B 17/1606 | 623/17.11 |
| 2006/0247640 A1* | 11/2006 | Blackwell | A61B 17/7068 | 606/71 |
| 2008/0161856 A1* | 7/2008 | Liu | A61B 17/7062 | 606/248 |
| 2008/0177272 A1* | 7/2008 | Zucherman | A61B 17/7068 | 606/90 |
| 2008/0183218 A1* | 7/2008 | Mueller | A61B 17/7068 | 606/280 |
| 2008/0275511 A1* | 11/2008 | Weinacker | A61B 17/8869 | 606/324 |
| 2009/0270918 A1* | 10/2009 | Attia | A61B 17/7062 | 606/248 |
| 2010/0087869 A1* | 4/2010 | Abdou | A61B 17/70 | 606/279 |
| 2010/0305619 A1* | 12/2010 | Knopfle | A61B 17/688 | 606/282 |
| 2011/0004248 A1* | 1/2011 | Abdou | A61B 17/7067 | 606/250 |
| 2011/0066186 A1* | 3/2011 | Boyer, II | A61B 17/7065 | 606/249 |
| 2011/0071568 A1* | 3/2011 | Ginn | A61B 17/7062 | 606/249 |
| 2011/0224731 A1* | 9/2011 | Smisson, III | A61B 17/7067 | 606/249 |
| 2011/0313458 A1* | 12/2011 | Butler | A61B 17/7065 | 606/249 |
| 2012/0136390 A1* | 5/2012 | Butler | A61B 17/7067 | 606/248 |
| 2012/0150228 A1* | 6/2012 | Zappacosta | A61B 17/7068 | 606/248 |
| 2012/0191135 A1* | 7/2012 | Abdou | A61B 17/7068 | 606/248 |
| 2012/0221050 A1* | 8/2012 | Ingalhalikar | A61B 17/7068 | 606/248 |
| 2013/0012996 A1* | 1/2013 | Zamani | A61B 17/7068 | 606/248 |
| 2013/0184753 A1* | 7/2013 | Keiper | A61B 17/7047 | 606/248 |
| 2013/0190820 A1* | 7/2013 | Siegfried | A61B 17/7068 | 606/248 |
| 2013/0296939 A1* | 11/2013 | Perkins | A61B 17/7068 | 606/249 |
| 2013/0296940 A1* | 11/2013 | Northcutt | A61B 17/7008 | 606/249 |
| 2014/0081331 A1* | 3/2014 | Zappacosta | A61B 17/7068 | 606/249 |
| 2014/0277143 A1* | 9/2014 | Zappacosta | A61B 17/7065 | 606/249 |
| 2015/0320456 A1* | 11/2015 | Field | A61B 17/7068 | 606/249 |

* cited by examiner

POLYAXIAL INTERSPINOUS FUSION IMPLANT AND BONE GROWTH STIMULATION SYSTEM

This claims priority to U.S. provisional patent application Ser. No. 62/009,129, filed Jun. 6, 2014, the entirety of which is incorporated herein by reference.

BACKGROUND

This invention relates generally to the field of spinal fusion surgery and more specifically to interspinous fusion implants and bone growth stimulation systems.

In 1986, the first interspinous device was introduced in Europe. It was the first dynamic stabilization system and consequently has the longest history at present. The device's original design was a titanium blocker that was inserted between adjacent processes and held in place with a polyester band wrapped around the spinous process above and below the blocker. After this first-generation device showed positive results, a second generation of interspinous implants were developed. The primary change was in the material used for the interspinous spacer. It was changed from titanium to polyetheretherketone (PEEK), a strong, plastic-like polymer that has more elasticity and is therefore less rigid than the previously used material. The implant has notches that fit the physiological shape of the lumbar spine.

Several devices currently exist that can be inserted between the spinous apophysis. Said devices have their antecedents in bone grafts placed between the spines more than fifty years ago. They were H-shaped and placed so that their ends surrounded the spines and their horizontal part was located between said spines in order to diminish the mobility among the vertebrae and achieve its final fusion. Likewise, there exist antecedents related to vertebral fusion which used different bow types, mostly metal bows to be linked to the spinous apophysis so that they become immobilized.

Newer technologies also exist that prohibit both flexion and compression between successive spinous processes. These devices are inserted between the spinous processes and contain barrel-like objects that maintain a space between the spinous processes thus prohibiting compression, while also containing successive plates with spikes that bore into successive spinal processes thus prohibiting flexion.

The problem with all of the known devices is their limited ability to adapt to the unique contours of each individual spinous process of each individual patient. This leads to reduction in the useful life of the implant after implantation and earlier failure than can be accomplished with an implant that adapts to the contours of the spinous between which it is implanted. This is important, because interspinous implants are meant to be long-term solutions that remain implanted for preferably the life of the subject who is treated with them. With life expectancy of people in developed countries exceeding 80 years of age and many people now living actively into their 90 s, these devices must maintain their functional integrity and must not fail for decades. Unfortunately, many of the current implants are prone to failure due to their inability to adapt to the shape of the specific spinous processes of the individual. What is needed are implants that adapt to the specific contours of each spinous process with which they are in contact, and that therefore remain firmly in place and maintain their functional integrity and are unlikely to suffer a mechanical failure for the life of the recipient of the implants.

Yet another problem is that most implants that prohibit compression and flexion require set screws and drivers to fix the components of the implants to the bone and fix the parts of the implant firmly in place relative to one another. This requires extra space to work in order to screw and unscrew. In addition, the single point of a set screw is tasked with maintaining the orientation of the parts of the device for as long as the device is in the body. All of the forces that pull and push the parts of the device toward and away from one another converge on the single set screw point that is tasked with maintaining the functional integrity of the device and prevent its failure. What is needed are devices that remain their functional integrity for long periods of time and are not prone to the limitations of using set screws.

SUMMARY

In one embodiment, a polyaxial interspinous fusion device is described. The polyaxial interspinous fusion device has a fixed anchor, a polyaxial anchor, and a bone spacer. The fixed anchor has a center ring, one or more fixed anchor arms projecting laterally from the center ring, and a barrel projecting transversely from the center ring. The polyaxial anchor has a socket ring and one or more polyaxial anchor arms projecting laterally from the socket ring, wherein the socket ring has a concave engagement surface. The bone spacer has a spacer head having a convex socket engagement surface that matches the concave engagement surface of the socket ring. The bone spacer also has one or more zip lock flanges extending transversely from the spacer head and one or more bone abutments extending transversely from the spacer head. The zip lock flanges and bone abutments of the bone spacer fit through the socket ring and the barrel of the fixed anchor fits through the socket ring. The zip lock flanges engage with the barrel when the zip lock flanges and bone abutments are inserted through the socket ring. When the polyaxial anchor engages with the spacer head, the polyaxial anchor has a polyaxial freedom of movement relative to the spacer head as a result of a ball and socket engagement between the concave engagement surface of the socket ring and convex socket engagement surface of the spacer head.

In another embodiment, an interspinous fusion device having a polyaxial anchor, a bone spacer, and a fixed anchor is described. The polyaxial anchor has a socket ring with a concave engagement surface. The bone spacer has a convex engagement surface, and the fixed anchor engages with the bone spacer by a zip-locking mechanism. The convex engagement surface of the bone spacer mates with the concave engagement surface of the polyaxial anchor to form a polyaxial engagement between the polyaxial anchor and the bone spacer.

Other objects and advantages of the present invention will become apparent from the following descriptions, taken in connection with the accompanying drawings, wherein, by way of illustration and example, various embodiments of the present invention are disclosed.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION

Exemplary embodiments of the invention are shown in the accompanying figures. FIGS. 1-11 depict one embodiment of a polyaxial interspinous fusion implant ("PISP") 100. PISP 100 is made of three interconnecting components that when assembled together form the PISP 100: a polyaxial anchor 110, a bone spacer 120, and a fixed anchor 181. Polyaxial anchor 110 and bone spacer 120 when mated together form polyaxial bone-spacing anchor 180. Each of implant components 110, 120 and 181 include subcomponents that will be described further.

Figure 1:
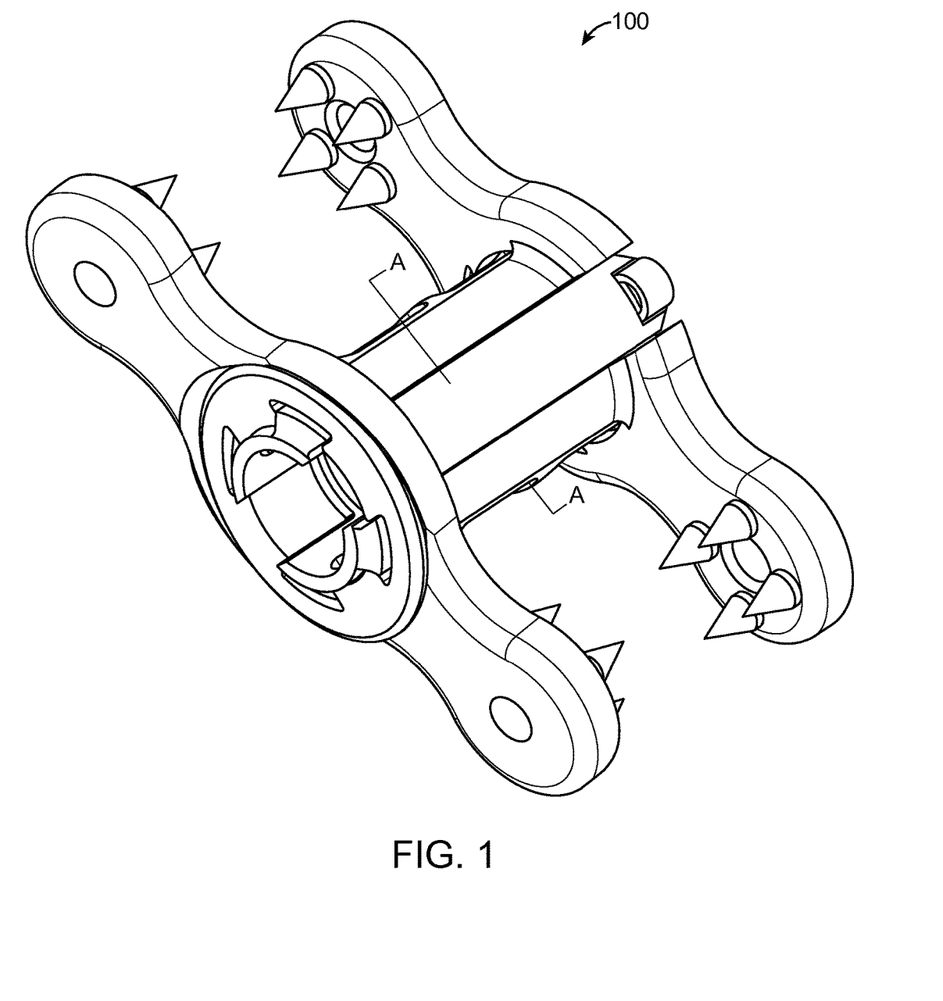
FIG. 1 is an isometric view of a polyaxial interspinous implant in an assembled state.
Figure 2:
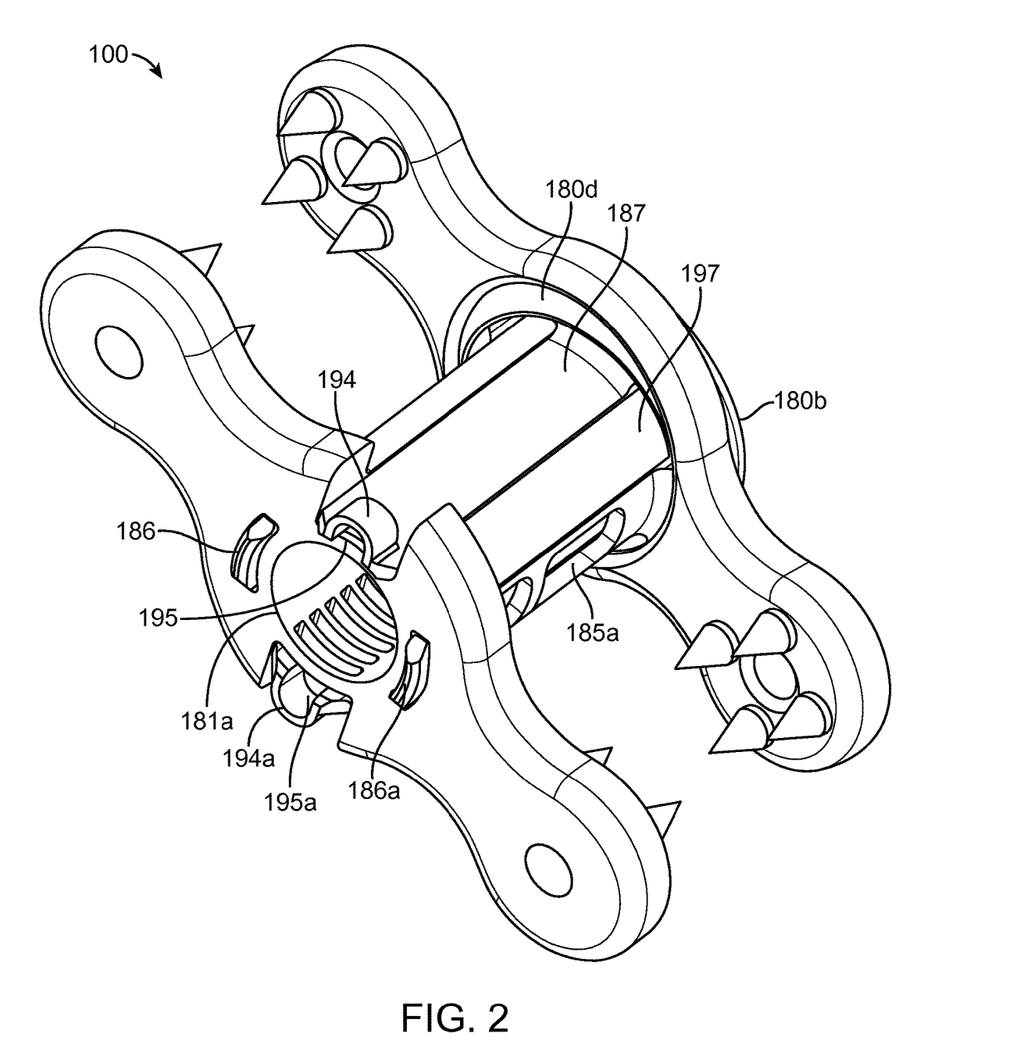
FIG. 2 is an isometric view of the polyaxial interspinous implant depicted in FIG. 1 in an assembled state with the polyaxial arm at a different angle.
Figure 3:
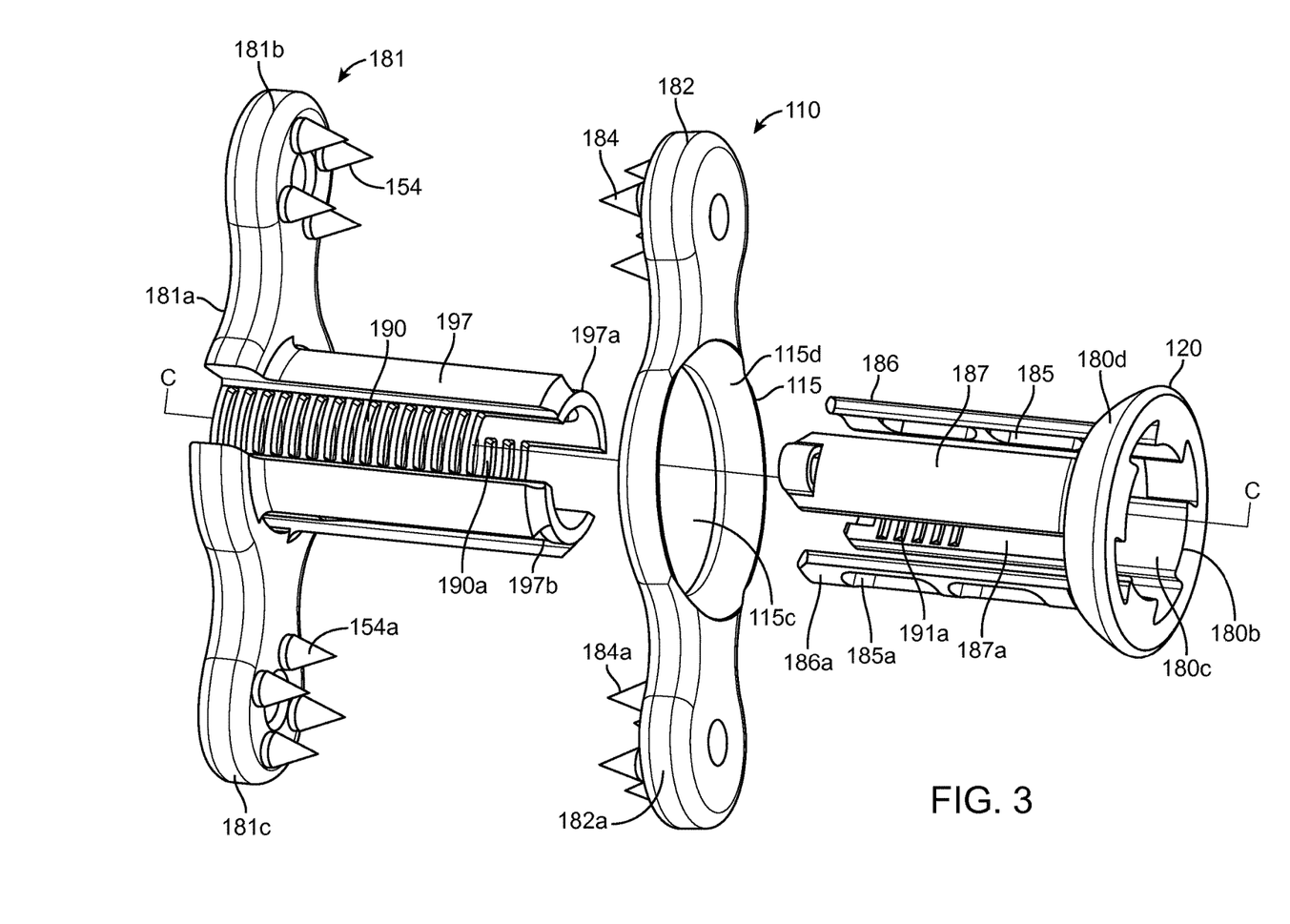
FIG. 3 is an exploded isometric view of the polyaxial interspinous implant depicted in FIG. 1.
Figure 4:
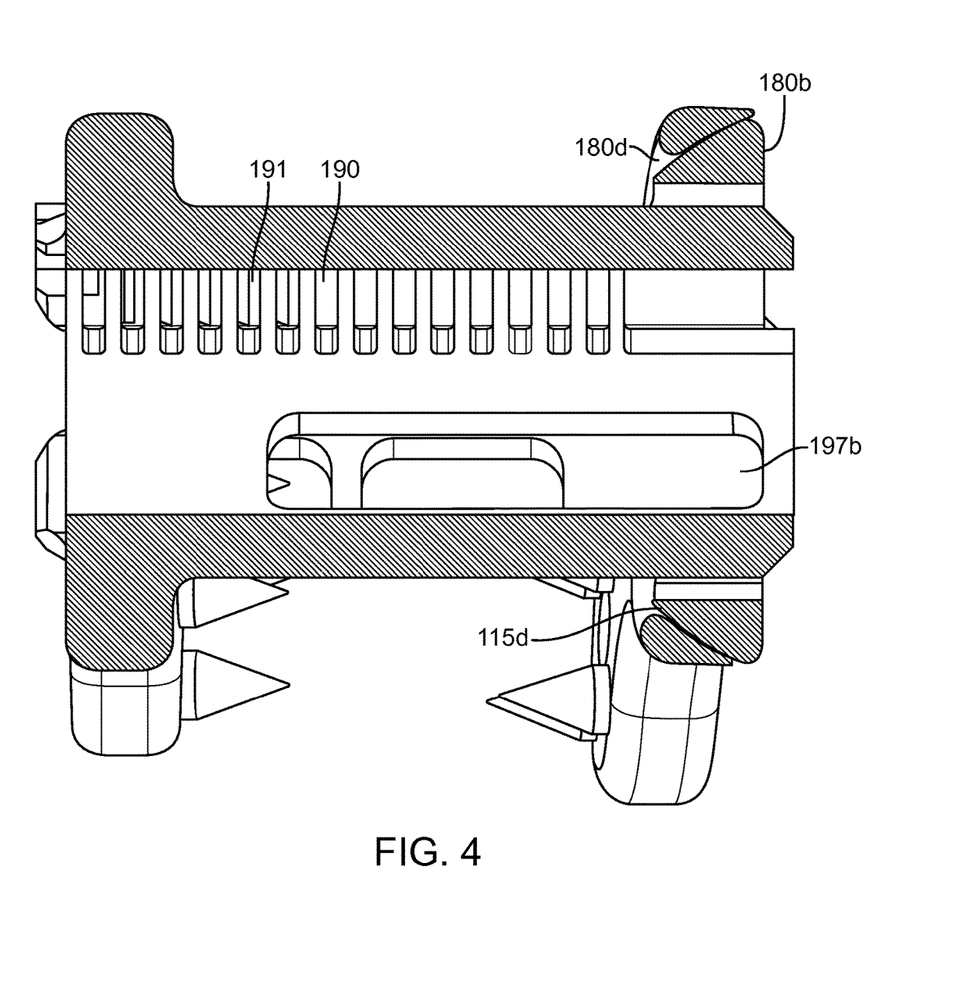
FIG. 4 is a cut-out view of the polyaxial interspinous implant of FIG. 1 along lines A-A.

Bone spacer 120 has a circular spacer head 180b. Spacer head 180b forms a round opening 180c through which various substances, such as bone grafts or natural or synthetic bone growth stimulating substances, such as synthetic or natural bone matrix, may be passed. Projecting transversely from the inner side of spacer head 180b and at a substantially 90° angle from spacer head 180b are two opposing zip lock flanges 187 and 187a, and two opposing bone abutments 186 and 186a. Alternatively, flanges 187 and 187a can be slightly biased inward toward each other for the purpose of forming a tight grip on barrel 197 of fixed anchor 181. A longitudinal axis extends from the center of spacer head 180b to the distal ends of zip lock flanges 187 and 187a and bone abutments 186 and 186a. Zip lock flanges 187 and 187a can be slightly curved along their width forming the same arc as the circular spacer head 180b from which they extend transversely. Zip lock flanges 187 and 187a are opposite each other and face each other as shown in FIGS. 2, 3, 5, 7, and 8. At the distal end of each of zip lock flanges 187 and 187a are one or more zip lock locking teeth 191 and 191a respectively that protrude from the inward facing surfaces of zip lock flanges 187 and 187a respectively. FIGS. 3 and 4 show that flanges 187 and 187a have five zip lock teeth, but it can be fewer or more than that number of teeth, such as 6, 7, 8, 9, 10 or more teeth. Each of zip lock teeth 191 and 191a form a top angled sliding face and a back locking ridge. The sliding face is angled to allow the teeth to slide forward and mate with the zip lock recesses or holes 190 and 190a respectively in lateral bone anchor 181. The back locking ridge of teeth 191 and 191a can form a substantially 90° angle with the zip lock flanges 187 and 187a or they can be angled toward spacer head 180b thus forming an acute angle between the back locking ridge and zip lock flanges 187 and 187a. If the angle is acute, then teeth 191 and 191a will be taller (i.e., they will extend further from their respective zip lock flange 187 and 187a) than when the angle is a substantially 90° angle for reasons that will be explained further below. The longer teeth will protrude through recesses 190 and 190a at an angle thus creating a force that pulls barrel 197 toward zip lock flanges 187 and 187a and prevents splaying of flanges 187 and 187a away from barrel 197. However, when the angle is substantially 90° and the walls forming the holes or recesses 190 and 190a are at 90°, then there is greater surface area contact between the back ridge of teeth 191 and 191a and the walls of recesses 190 and 190a respectively, which increases the forces between teeth 191 and 191a and their respectively mated recesses 190 and 190a. The 90° configuration also reduces the risk of teeth breaking since the pressure on the back ridge is spread out across the entire surface area of the ridge rather than on just the narrow strip that makes contact with the edges of recesses 190 and 190a. Teeth 191 and 191a lock bone spacer 120 and barrel 197 longitudinally, radially, and transversely with respect to one another due to the forces between teeth 191 and 191a and recesses 190 and 190a into which they slide.

The outward facing surfaces of zip locking flanges 187 and 187a are substantially smooth. At the distal end of the top surface of each of zip lock flanges 187 and 187a are release nubs 194 and 194a respectively, which contain holes 195 and 195a respectively. A release tool can be inserted into each of holes 195 and 195a to bend flanges 187 and 187a away from barrel 197, thus pulling teeth 191 and 191a out of recesses 190 and 190a respectively.

Bone abutments 186 and 186a face each other and extend transversely from spacer head 180b. They can both be slightly rounded along their width thus forming the same arc as circular spacer head 180b from which they extend transversely. Each of bone abutments 186 and 186a has one or more fusion windows 185 and 185a respectively. In the embodiment shown in the Figures, each bone abutment 186 and 186a is shown with two fusion windows 185 and 185a respectively. Fusion windows 185 and 185a allow fusion between adjacent spinous processes through the barrel formed by the connection between the lateral bone anchor 181 and the second component 120. The outer facing surface of bone abutments 186 and 186a may be smooth. Alternatively, they may be roughened to form more friction between bone abutments 186 and 186a and the spinous processes which they respectively abut. Increased friction will minimize any movement between the spinous processes and PISP 100 once PISP 100 is implanted between adjacent spinous processes.

Spacer head 180b can have a flat outer head surface and a rounded or convex tapered inner engagement surface 180d similar to a countersunk flat top screw. The convex engagement surface 180d of spacer head 180b of component 120 is shaped to engage in a ball and socket formation with inner engagement surface 115d of socket ring 115 of polyaxial anchor 110. Due to the ball and socket engagement between the engagement surface 115d of socket ring 115 and convex engagement surface 180d of spacer head 180b of bone spacer 120, polyaxial anchor 110 can be polyaxially engaged with bone spacer 120.

Polyaxial anchor 110 contains a socket ring 115 having a concave engagement surface 115d. Socket ring 115 forms a hole 115c through which bone spacer 120 can be inserted. Extending laterally in one direction from socket ring 115 is superior polyaxial anchor arm 182. Extending laterally in the exact opposite direction from socket ring 115 is inferior polyaxial anchor arm 182a. Both superior and inferior polyaxial anchor arms 182 and 182a can be circular in shape for optimum anchoring capacity to the spinous process. In one embodiment, superior and inferior polyaxial anchor arms 182 and 182a are the same shape and size. In other embodiments, they are different shapes and/or sizes. In one embodiment, a straight line runs through the center of each of polyaxial anchor arms 182, 182a and socket ring 115, i.e., they are at an angle of 180° from one another as shown in FIG. 3. The distance between the ends of superior and inferior polyaxial anchor arms 182 and 182a can be between about 30 mm and about 50 mm. In one embodiment, it is between about 35 mm and about 40 mm. In other embodiments, it is about 30 mm, 35 mm, 40 mm, 45 mm or 50 mm.

Each of polyaxial anchor arms 182 and 182a contain one or more (four as shown in the Figures) spikes 184 and 184a respectively that can penetrate bone. Spikes 184 and 184a protrude transversely in an inward direction from polyaxial anchor arms 182 and 182a. Spikes 184 and 184a are designed to penetrate the bone of the spinous process. While spikes 184 penetrate one spinous process, spikes 184a penetrate the next spinous process inferior to the one being penetrated by spikes 184. In addition, superior and inferior polyaxial anchor arms 182 and 182a may be made of a unibody construction with socket ring 115, or alternatively, they may be secured to arms projecting from socket ring 115 by pins or other means that permit superior and inferior polyaxial anchor arms 182 and 182a to freely pivot at an angle relative to socket ring 115.

Fixed anchor 181 has a center ring 181a. Extending laterally in one direction from center ring 181a is superior fixed anchor arm 181b. Extending laterally in the exact opposite direction from center ring 181a is inferior fixed anchor arm 181c. Both superior and inferior fixed anchor arms 181b and 181 c can be circular in shape for optimum anchoring capacity to the spinous process. In one embodiment, superior and inferior fixed anchor arms 181b and 181c are the same shape and size. In other embodiments, they are different shapes and/or sizes. In one embodiment, a straight line runs through the center of each of fixed anchor arms 181b, 181c and center ring 181a, i.e., they are at an angle of 180° from one another as shown in FIG. 3. The distance between the ends of superior and inferior fixed anchor arms 181b and 181c can be between about 30 mm and about 50 mm. In one embodiment, it is between about 35 mm and about 40 mm. In other embodiments, it is about 30 mm, 35 mm, 40 mm, 45 mm or 50 mm. In one embodiment the distance between the ends of superior and inferior fixed anchor arms 181b and 181c is the same as the distance between polyaxial anchor arms 182 and 182a.

Each of fixed anchor arms 181b and 181 c contain one or more (four as shown in the Figures) spikes 154 and 154a respectively that can penetrate bone. Spikes 154 and 154a protrude transversely in an inward direction from fixed anchor arms 181b and 181c. Spikes 154 and 154a are designed to penetrate the bone of the spinous process. While spikes 154 penetrate one spinous process, spikes 154a penetrate the next spinous process inferior to the one being penetrated by spikes 154. In addition, superior and inferior fixed anchor arms 181b and 181c may be made of a unibody construction with center ring 181a, or alternatively, they may be secured to arms projecting from center ring 181a by pins or other means that permit superior and inferior fixed anchor arms 181b and 181c to freely pivot at an angle relative to center ring 181a.

Center ring 181a forms a round opening 181d through which various substances, such as natural or synthetic bone grafts or bone growth stimulating substances such as natural or synthetic bone matrix, may be passed.

Center ring 181a has holes 189 and 189a that are arcuate and are shaped and sized to receive the distal ends of the bone abutments 186 and 186a respectively. Holes 189 and 189a are opposite each other on the center ring 181a. When bone abutments 186 and 186a mate respectively with holes 189 and 189a, barrel 197 and bone spacer 120 are prevented from spinning relative to one another, and they become locked radially in place with respect to one another (see FIG. 8). Center ring 181a also has slots 189c and 189d that are arcuate and are shaped and sized to receive the distal ends of zip lock flanges 187 and 187a respectively (see FIG. 5).

Figure 5:
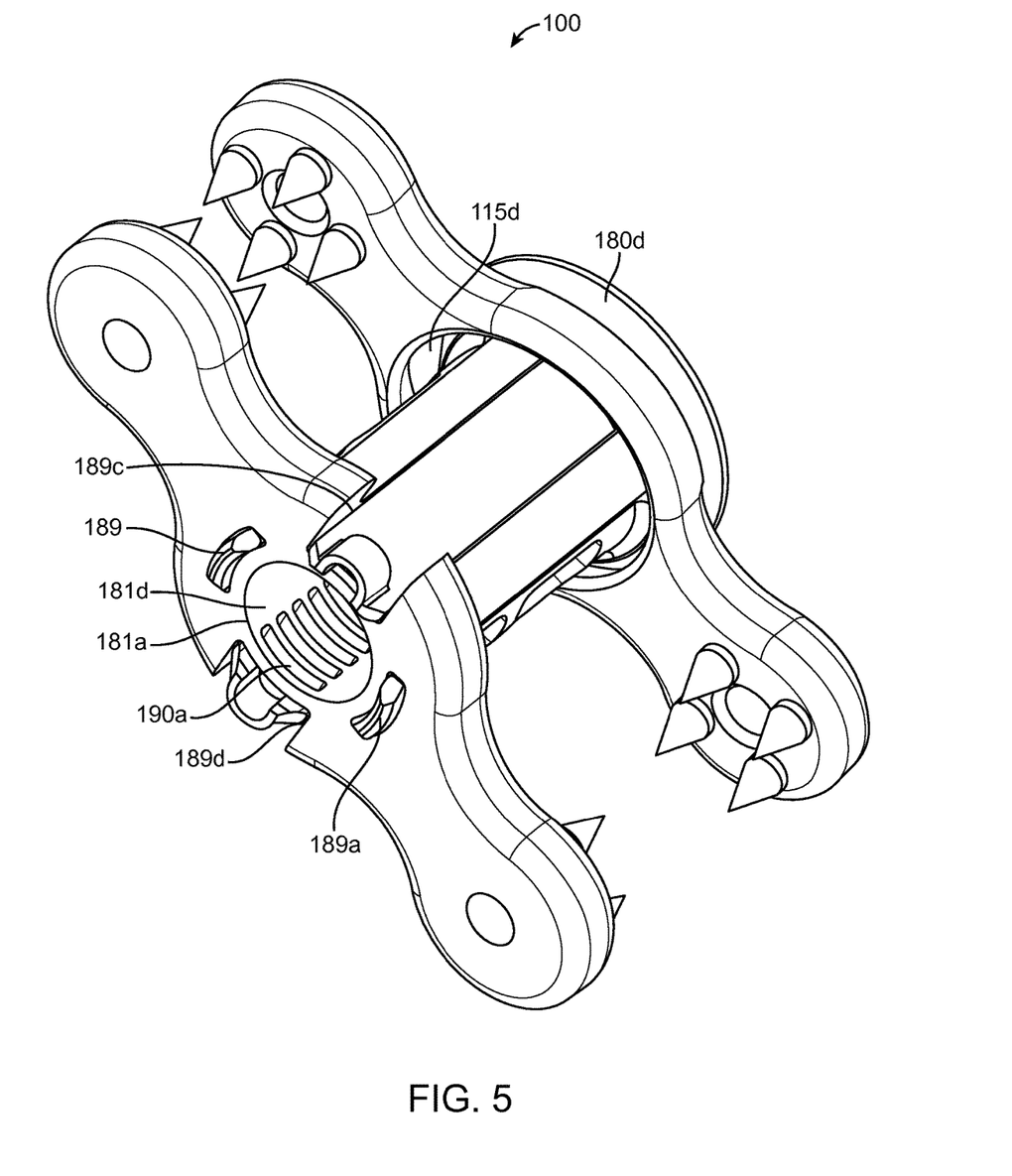
FIG. 5 is another isometric view of the polyaxial interspinous implant depicted in FIG. 1, as viewed from another angle.
Figure 6:
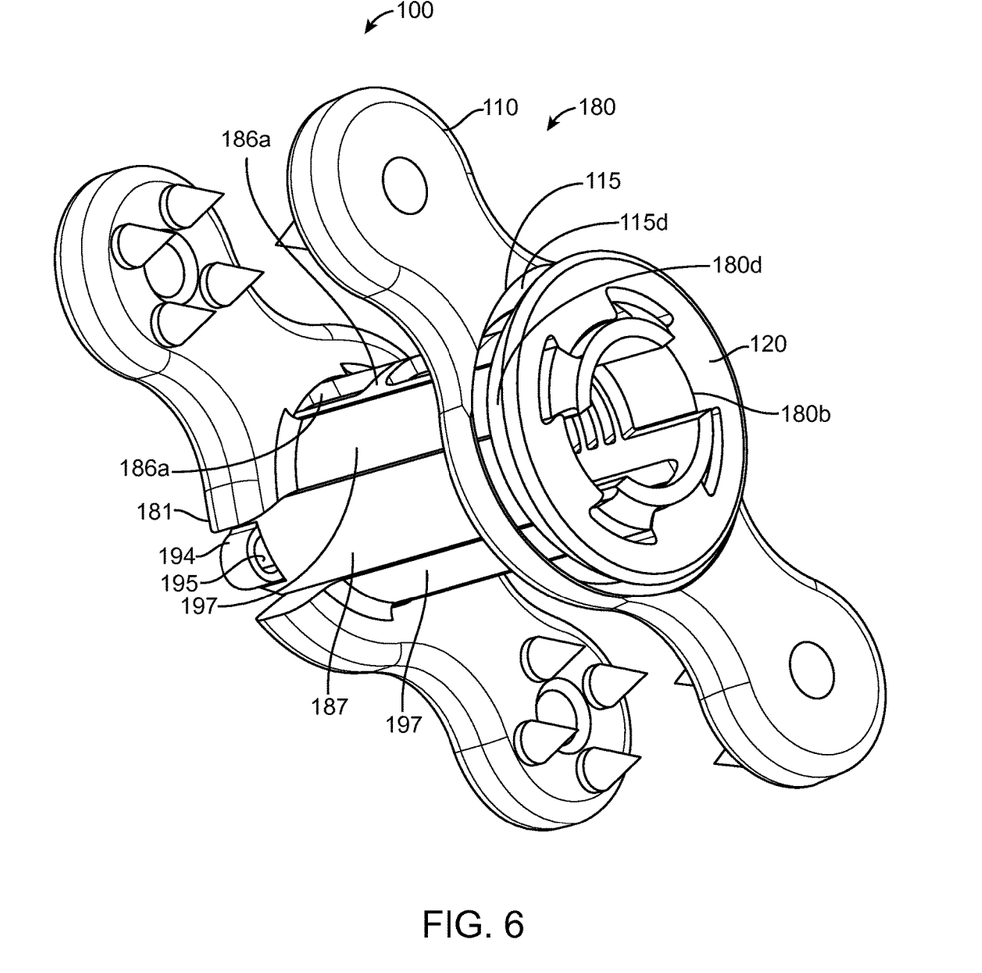
FIG. 6 is yet another isometric view of the polyaxial interspinous implant depicted in FIG. 1, as viewed from yet another angle.

Projecting transversely from the inner side center ring 181a of fixed anchor 181 and at a substantially 90° angle from center ring 181a is a barrel 197. Barrel 197 can have a diameter of between about 5.0 mm and about 25 mm. In various embodiments, it has a diameter of about 5.0 mm, 6.0 mm, 7.0 mm, 8.0 mm, 9.0 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm or 25 mm. The length of barrel 197 can be between about 15 mm and about 30 mm. In various embodiments, it has a length of about 15 mm, 16 mm, 17 mm, 18 mm, 19 mm, 20 mm, 21 mm, 22 mm, 23 mm, 24 mm, 25 mm, 26 mm, 27 mm, 28 mm, 29 mm or 30 mm. Barrel 197 contains two columns of zip lock recesses 190 and 190a. Zip lock recesses 190 are opposite zip lock recesses 190a on barrel 197. The column of zip lock recesses 190 is aligned with slot 189c, and the column of zip lock recesses 190a is aligned with slot 189d. Zip lock recesses 190 receive and mate with teeth 191 of zip lock flange 187, and zip lock recesses 190a receive and mate with teeth 191a of zip lock flange 187a. In on embodiment, as shown in FIGS. 2 and 5, zip lock recesses 190 and 190a are elongated holes or slits that are shaped to receive teeth 191 and 191a respectively. In another embodiment (not shown in the figures) zip lock recesses 190 and 190a are formed by protruding teeth that extend radially outward from barrel 197. Such teeth can be angled or sloped in the opposite direction of teeth 191 and 191a so that teeth 191 and 191a will slide over teeth 190 and 190a respectively when bone spacer 120 and fixed anchor 181 are forced into engagement with each other. When teeth 191 and 191a engage with teeth 190 and 190a respectively bone spacer 120 80 cannot be pulled apart from barrel 197 of fixed anchor 181, because the vertical back side of teeth 191 and 191a will catch against the vertical front side of teeth 190 and 190a respectively. In yet another embodiment, zip-lock recesses are formed by straight vertical protuberances over which teeth 191 and 191a slide. When teeth 191 and 191a engage with vertical protuberances 190 and 190a respectively bone spacer 120 cannot be pulled apart from barrel 197 of fixed anchor 181, because the vertical back side of teeth 191 and 191a will catch against the vertical protuberances 190 and 190a respectively. Barrel 197 also has windows 197a and 197b that are opposite one another on barrel 197. Windows 197a and 197b are the same size and shape as windows 185 and 185a and align with windows 185 and 185a respectively when barrel 197 of fixed anchor 181 is mated with bone spacer 120.

Components 181, 120 and 110 are assembled with one another in the following manner to form polyaxial interspinous fusion implant PISP 100. Flanges 187 and 187a and abutments 186 and 186a are inserted through hole 115c of socket ring 115 through the side of the polyaxial anchor 110 that contains the engagement surface 115d of the socket ring 115. Meanwhile, barrel 197 of fixed anchor 181 is brought into coaxial alignment with flanges 187 and 187a and abutments 186 and 186a. Flanges 187 and 187a are guided over the columns of zip lock recesses 190 and 190a respectively until column of zip lock teeth 191 engages with column of zip lock recesses 190 and column of zip lock teeth 191a engages with column of zip lock recesses 190a. Once teeth 191 and 191a engage with recesses 190 and 190a respectively, fixed anchor 181 becomes locked to bone spacer 120, and cannot be unlocked or disengaged without a splaying tool that splays flanges 187 and 187a away from columns of recesses 190 and 190a respectively. Bone spacer 120 is pushed toward center ring 181a and columns of teeth 191 and 191a will slide over columns of recesses 190 and 190a respectively given the orientation and shape of the teeth, but once teeth 191 and 191a engage with recesses 190 and 190a respectively, bone spacer 120 cannot be pulled back in a direction away from center ring 191a without a splaying tool to splay flanges 187 and 187a away from barrel 197.

As flanges 187 and 187a glide over barrel 197, bone abutments 186 and 186a glide over barrel 197 as well, and windows 185 and 185a become aligned respectively with windows 197a and 197b of barrel 197. Barrel 197 thus becomes nested within bone abutments 186 and 186a and flanges 187 and 187a of bone spacer 120, such that barrel 197 becomes radially nested within bone spacer 120 (see e.g., FIG. 2). Once windows 185 and 185a are aligned with windows 197a and 197b respectively, a barrel is formed by the mating of fixed anchor 181 and bone spacer 120 with opposing windows (185 and 197a form one window while 185a and 197b form another) through which bone can grow, such that bone from one spinous process can eventually fuse with bone from the adjacent spinous process through the windows. In addition, bone growth stimulating materials, such as natural or synthetic bone matrix or bone graft material, can be inserted through either of openings 180c or 181d into barrel 197 to help stimulate the growth of bone between the adjacent spinous processes.

Thus, bone spacer 120 can slide over barrel 197 and become reversibly locked (but only unlocked with a splaying tool) without any additional tools, but the two components cannot be separated from one another once they are engaged without a release tool that splays zip-lock flanges 187 and 187a radially apart from barrel 197. This results in PISP 100 being a device that can be locked to the spinous processes without a set screw or screw drivers or the need for any additional locking tools that require adjustment of screws. Components 120 and 181 need only be pushed or forced together and they will form a tight lock to one another that is not prone to failure and is only reversible with a splaying tool. The columns of multiple or a series of teeth 191 and 191a mating with multiple or a series of recesses 190 and 190a respectively prohibits the migration of component 181 away from component 120 once the two components are engaged to one another through the described zip-locking mechanism, and this minimizes the risk of long-term mechanical failure of PISP 100 once it has been implanted.

Components 110, 120 and 181 mate with one another to form a single ISP unit that not only separates two adjacent spinous processes from one another at a predetermined distance, but keeps them locked with respect to one another as a result of the penetration of the spinous processes by the anchoring spikes (described above). The bone abutments 186 and 186a thus prevent extension between adjacent spinous processes, while the anchors prevent flexion between two adjacent spinous processes.

Figure 10:
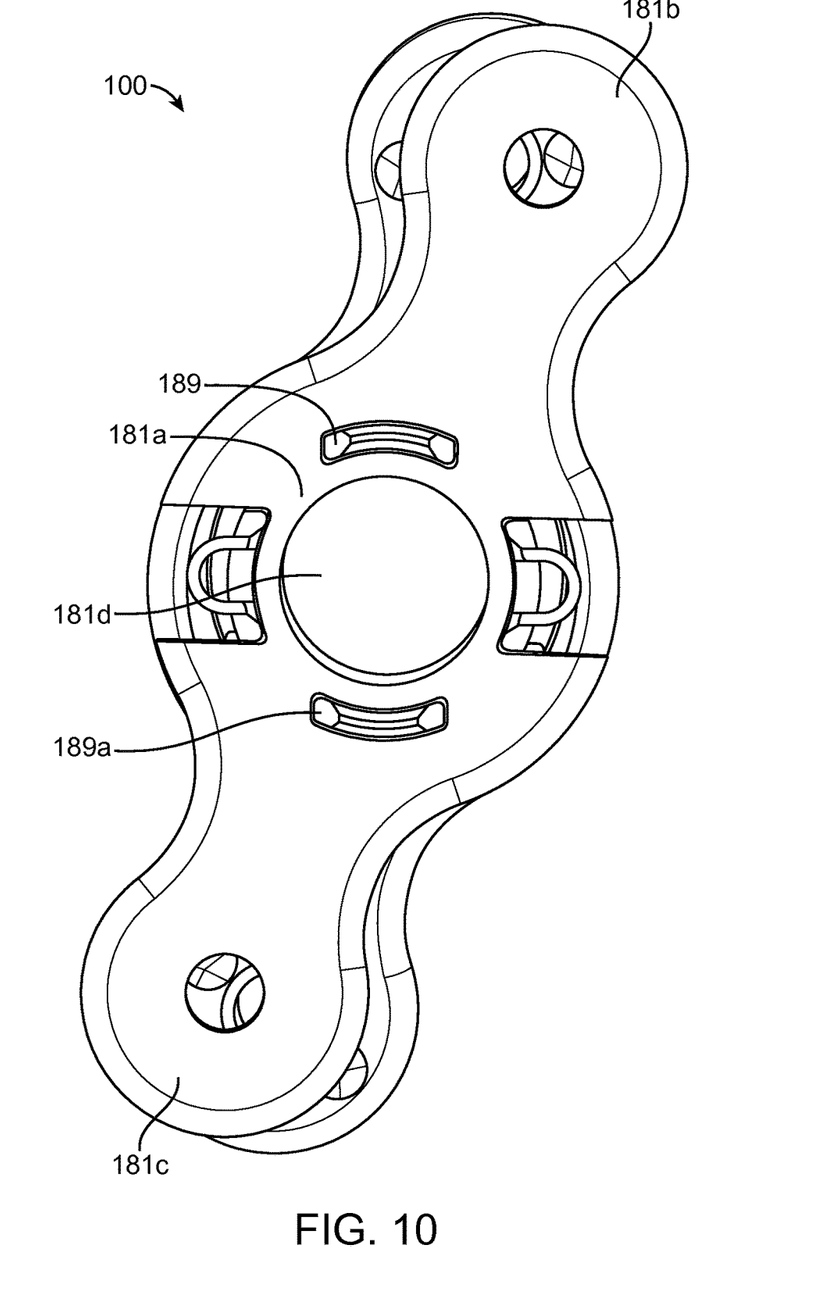
FIG. 10 is a side view of the polyaxial interspinous implant depicted in FIG. 1, as viewed from non-dynamic arm of the implant.
Figure 11:
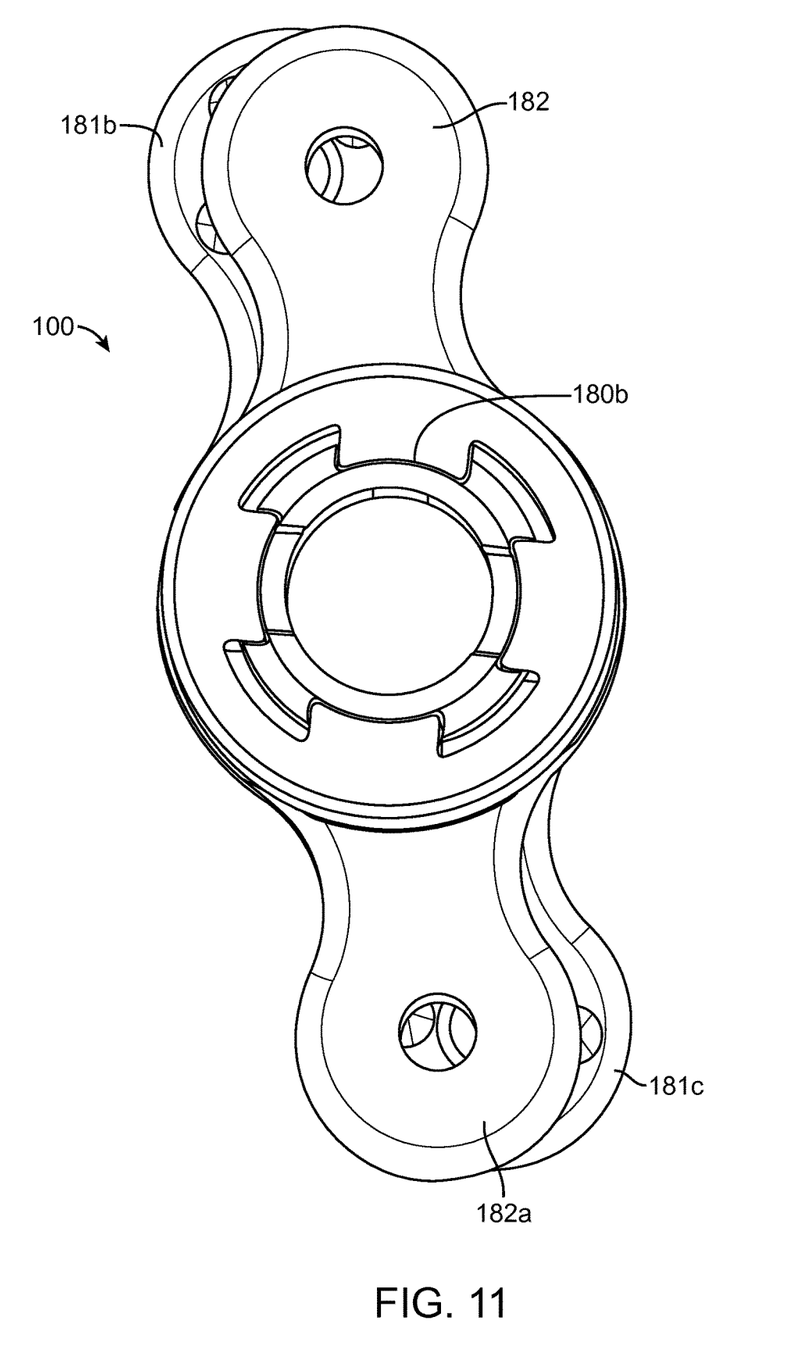
FIG. 11, is a side view of the polyaxial interspinous implant depicted in FIG. 1, as viewed from the polyaxial arm of the implant.

One significant improvement over older interspinous fixation devices is that PISP 100 not only adapts to the shape and curvature of each particular spinous processes to which anchors 182, 182a, 181b and 181c become affixed, but PISP 100 also adapts to misalignments between adjacent spinous processes as a result of the polyaxial engagement between polyaxial anchor 110 and bone spacer 120. Polyaxial anchor 110 can spin around barrel 197 and also around flanges 187 and 187a and abutments 186 and 186a. Thus, when bone spacer 120 is coupled to fixed anchor 181 through hole 115c, because hole 115c is round, polyaxial anchor 110 can spin 360° about axis formed by line C-C of FIG. 3, and this allows polyaxial anchor 110 to spin around barrel 197 when it is coupled to bone spacer 120. Thus, polyaxial anchor arms 182 and 182a can be offset as much as 180° from their corresponding fixed anchor arms 181b and 181c respectively. FIGS. 10 and 11 depict an orientation in which an offset is clearly shown.

Figure 7:
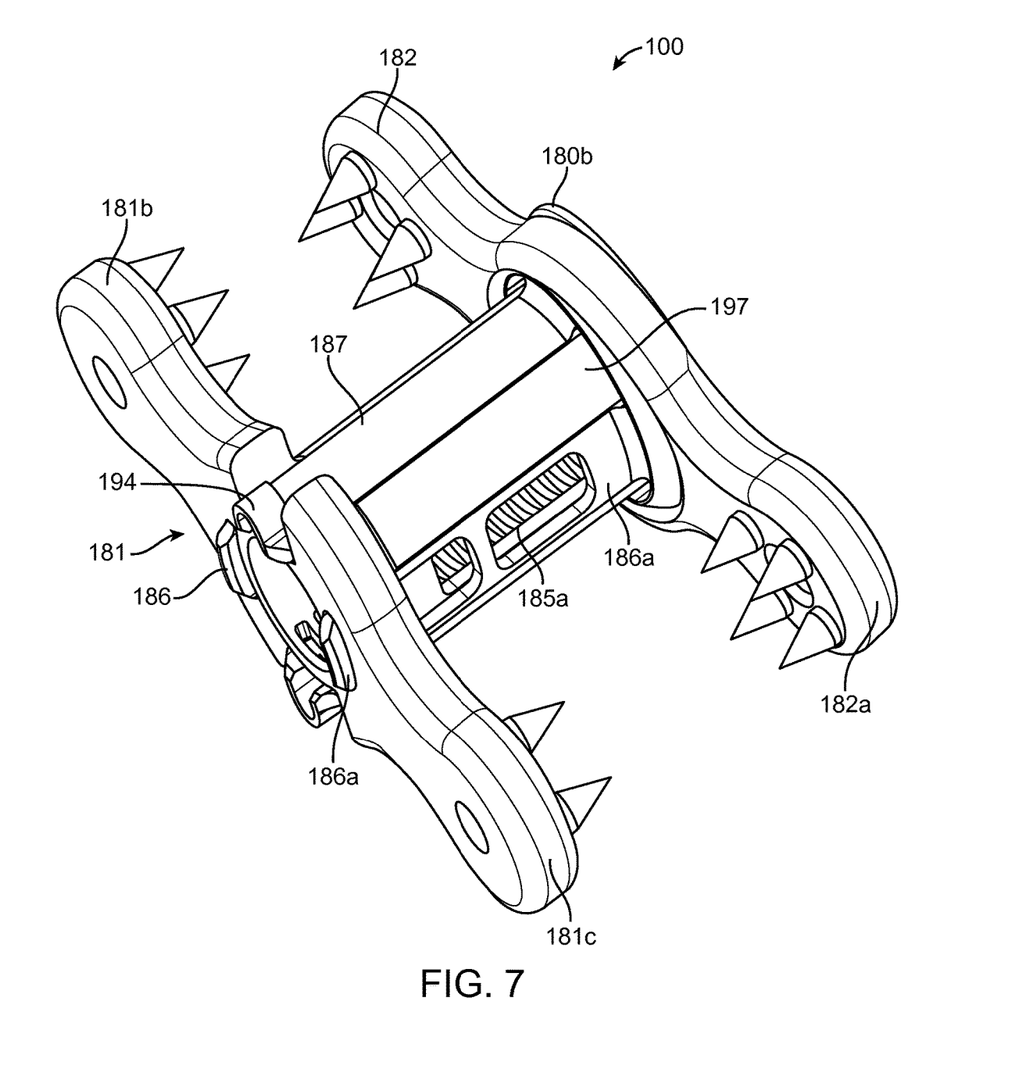
FIG. 7 is yet another isometric view of the polyaxial interspinous implant depicted in FIG. 1, as viewed from yet another angle.
Figure 8:
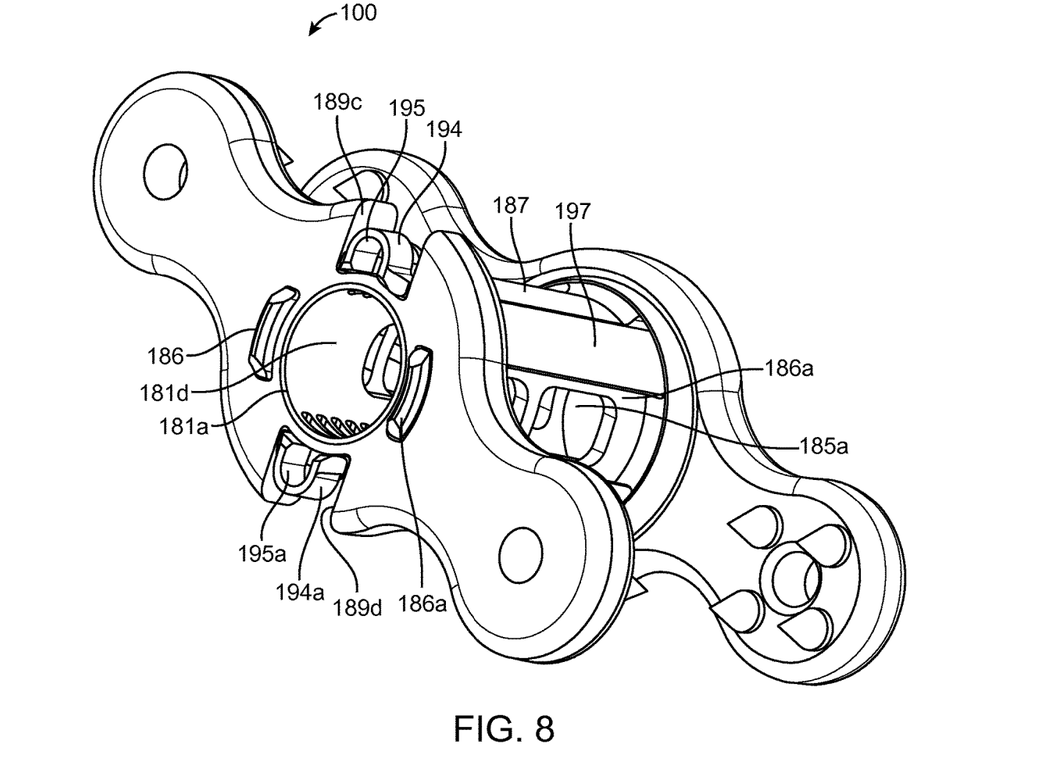
FIG. 8 is yet another isometric view of the polyaxial interspinous implant depicted in FIG. 1, as viewed from yet another angle.
Figure 9:
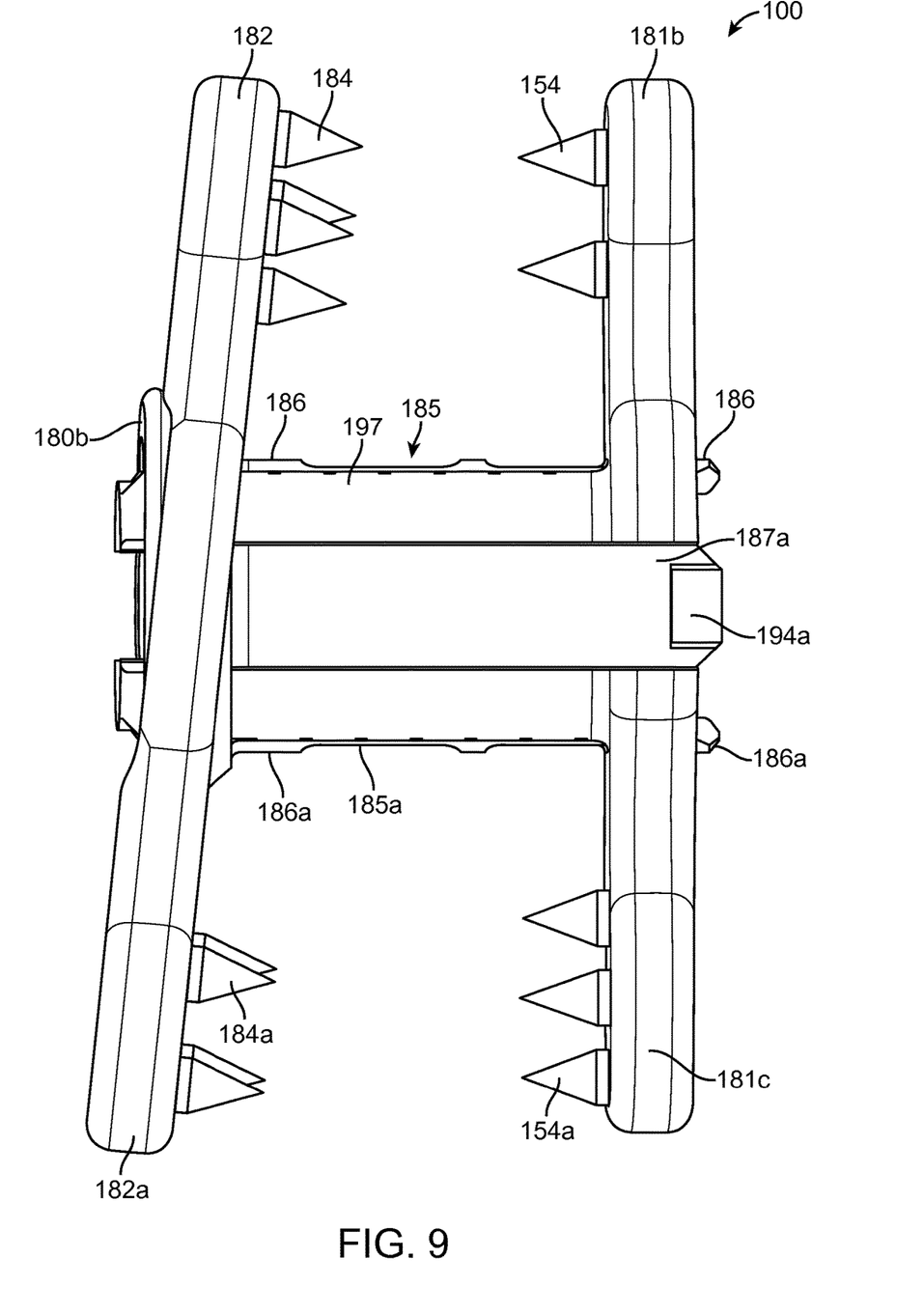
FIG. 9 is a top view of the polyaxial interspinous implant depicted in FIG. 1.

In addition, due to the ball and socket connection between concave engagement surface 115d of socket ring 115 and the convex surface 180d of bone spacer 120, polyaxial anchor 110 can be tilted at any angle relative to fixed anchor 181. An example of that is shown in FIGS. 7 and 9. Thus, the polyaxial anchor 110 can be polyaxial rotated or tilted in any direction while bone spacer 120 is fixed to fixed anchor 181 in a manner that does not permit bone spacer 120 and fixed anchor 181 to rotate axially with respect to one another or slide away from one another. This is a key feature of the present invention, because it easily and conveniently allows PISP 100 to adapt itself to any angle, slope or shape of any spinous process and adapt itself to any misalignment between adjacent spinous processes. The ball and socket engagement of the polyaxial anchor 110 to the bone spacer 120 allows the polyaxial anchor to tile in any direction relative to the bone spacer.

In one method of implantation, the assembled PISP 100 can be inserted between two spinous processes of adjacent vertrebrae in an anterior to posterior direction after severing spinous ligaments to remove them from the path of implantation. In another method of implantation, no spinous ligaments are severed and fixed anchor 181 and bone spacer 120 are separated and can each individually be inserted from opposing lateral directions toward each other anterior to the undisturbed spinous ligaments while polyaxial anchor 110 is placed adjacent one side of successive spinous processes opposite the fixed anchor. Barrel 197 is inserted through the space between two successive spinous processes with fixed anchor 181 placed adjacent, e.g., the left side of a superior spinous process and fixed anchor 181c placed adjacent the left surface of the spinous process immediately inferior to the first spinous process. The flanges 187 and 187a and abutments 186 and 186a are inserted through hole 115 of polyaxial anchor 110. Polyaxial anchor arm 182 is placed adjacent the right surface of the spinous process across from fixed anchor 181b, and polyaxial anchor arm 182a is placed adjacent the right surface of the spinous process immediately inferior to the first spinous process across from fixed anchor 181c. Bone spacer 120 and fixed anchor 181 are squeezed toward one another so that flanges 187 and 187a engage with barrel 197 as described above, and bone spacer 120 and fixed anchor 181 are squeezed toward one another until convex engagement surface 180d of bone spacer 120 pushes against the concave engagement surface 115d. Squeezing continues until spikes 154 and 154a firmly penetrate the left side of the successive and respective spinous processes while spikes 184 and 184a firmly penetrate the right side of the same successive and respective spinous processes. As that occurs, the ball and socket engagement between polyaxial anchor 110 and spacer head 180b of bone spacer 120 will automatically force polyaxial anchor 110 to rotate and spin to form the most advantageous engagement of spikes 184 and 184a with the spinous processes with which they engage. No matter what the angle and shape of the two successive spinous processes and no matter how they are aligned or misaligned with one another, polyaxial anchor 110 will spin and tilt automatically as the PISP 100 is locked in place. With the penetration of spikes 184, 184a, 154 and 154 into the spinous processes, PISP 100 prohibits both extension (as a result of bone abutments 186 and 186a abutting the inner spinous process) and flexion (as a result of the anchoring by the spikes).

Disengagement of PISP 100 from the spinous processes requires a two simultaneous forces: pulling flanges 187 and 187a apart from one another (a radial spreading force) with a separator while simultaneously pulling components 120 and 181 longitudinally away from one another (a longitudinal pushing or pulling force). The likelihood of both forces occurring at the same time inadvertently or through failure of PISP 100 over time are much lower than devices that use set screws, where the screw can become undone over time and then subsequent movement of the two parts away from each other can happen at a later time thus causing a failure of the device in situ. This type of locking mechanism is also a significant improvement over a simple ratchet, because a ratchet does not create the firm grip and increased forces created by the engagement of a series of successive teeth with a series of successive recesses.

In addition, the unique polyaxial capability of PISP 100 creates a much better grip and connection between PISP 100 and the spinous processes than older devices that are incapable of conforming to the shape, size, angle and slope of spinous processes and the natural misalignment that exists between successive spinous processes.

PISP 100 can be packaged as part of a kit that comes with an implantation tool that controls the insertion of PISP 100 between spinous processes and a removal tool that is designed to splay the flanges 187 and 187a away from barrel 197 so that the two components 120 181 can be separated from one another. The implantation tool can be a compression tool that engages indentations on the opposing arms 182 and 182a on the one hand and the outer flat surface of spacer head 180b on the other hand, and squeezes the two components 120 and 181 together forcing the flanges 187 and 187a to advance forward over the zip-lock recess columns 190 and 190a respectively and toward and through openings 189c and 189d respectively. The kit can also include synthetic or natural bone matrix that can be used with PISP 100 to promote fusion between successive vertebrae. The bone matrix can be packed in the barrel 197 promoting bone growth between a superior vertebra and an inferior vertebra through windows 185, 185a, 197a, and 197b. Such a kits can also come with instructions for use. The instructions for use can include the following steps, which can be part of a method of implanting PISP 100:

i. Remove components 110, 120 and 181 of PISP 100 from packaging
ii. Insert component 120 through the hole of component 110.
iii. Manually align the zip-lock flanges with zip-lock recess columns respectively.
iv. Manually guide zip-lock flanges over zip-lock recess columns of the barrel until at least one of the teeth of each of the zip-lock flanges respectively engages at least one of the recesses of the zip-lock recess columns respectively.
v. Pack the barrel (this refers to barrel 97) with bone growth matrix (this step can be performed after PISP is implanted as well).
vi. Implant the assembled PISP 100 by guiding the zip-locked section between adjacent spinous processes while the arms of the one component are aligned with the outer sides of the two adjacent spinous processes and the other arms of the other component are aligned with the opposite outer sides of the same two adjacent spinous processes.
vii. Adjust the angle of PISP 100 so that it is implanted in the orientation desired.
viii. Engage the implantation tool to the indentations on the outer sides of the arms of the fixed anchor or component 181 on the one hand and the ring of the bone spacer or component 120 on the other. Cause the implantation tool to squeeze the two components toward each other forcing the flanges to advance forward over the zip-lock recess columns and toward and through openings at the opposite ends (180° apart) of the barrel that receive the ends of the flanges.
ix. Cease causing the implantation tool to squeeze the two components together once the spikes on the arms of the fixed anchor 181 and the spikes on the arms of the polyaxial anchor 110 have firmly engaged the bone on opposite sides of the adjacent spinous processes and have burrowed into the bone with the head of the bone spacer 120 firmly pushing against the engagement ring of the polyaxial anchor 110.
x. Check to make sure that the PISP is firmly anchored to the successive spinous processes.
xi. To remove a PISP 100 use the removal tool to splay flanges on the bone spacer 120 away from the barrel of the fixed anchor 181 thus disengaging teeth on the flanges from the recesses on the barrel, and pull the two components away from each other until they are disengaged from one another.

Another aspect of the present invention involves bone growth stimulation. Pulsed electromagnetic field therapy (PEMFT), also called pulsed magnetic therapy, pulse magnetotherapy, or PEMF, is a reparative technique most commonly used in the field of orthopedics for the treatment of non-union fractures, failed fusions, congenital pseudarthrosis and depression. In the case of bone healing, PEMF uses electrical energy to direct a series of magnetic pulses through injured tissue whereby each magnetic pulse induces a tiny electrical signal that stimulates cellular bone repair. It is believed that PEMF therapy causes biochemical changes at the cellular level to accelerate bone formation.

Bone growth stimulation by PISP 100 is achieved by making it of a specific material. All or some of the components of PISP 100 can be made of pyrolitic carbon or coated with varying depths of a pyrolitic carbon surface.

Pyrolitic carbon is a structural carbon coating that is most often deposited on high density, high purity graphite pre-form. Other substrate pre-forms can also be used such as high melting point metals. The surface of pyrolitic carbon can be polished to a high gloss where articulation or thrombo-resistance is required. Alternatively, the surface can be left in an as deposited state providing some surface topography for bone and or tissue on-growth. Pyrolitic carbon is highly conductive and highly diamagnetic, making it an excellent material to receive a wireless signal, such as a radio-frequency or magnetic signal inducing it to emit a magnetic field.

An external transmitter can be used to transmit a wireless signal to PISP 100 (can also be ISP 200, ISP 285, ISP 300, system 1000 or assembly 1200 or any other implant disclosed herein), interbody vertebral spacer 4000 or femur implant 3000. Some or all of the components of PISP 100 can have a surface that is coated to varying depths of pyrolitic carbon deposited on a high purity graphite pre-form or another type of high melting point metal. The wireless signal transmitted by the transmitter can be a magnetic frequency signal, a radio frequency signal, or any other type of wireless signal that can be received by implant PISP 100. In one embodiment, PISP 100 can be implanted and packed with bone growth material, such as synthetic or natural bone matrix. In addition, it has a pyrolitic carbon surface that can be smooth or porous. A porous surface will promote bone on-growth on the surface. During normal use it acts as an ISP. However, when it receives a wireless signal from the external transmitter the pyrolitic carbon surface acts as a conductor for that signal and it emits a magnetic field to the areas around it. The emission of magnetic field to the bone around PISP 100 stimulates bone growth of the native bone and enhances the activity of the packed bone matrix. Thus, PISP 100 acts as a bone growth stimulator and promotes fusion when it is activated by the external wireless transmitter.

Another problem addressed herein is that implants ideally should have a modulus of elasticity that is similar to the bone at the implant site. When an orthopedic implant is placed in the body to replace a bone or a part of a bone, it needs to handle the loads in the same way as its surrounding bone. If the modulus of elasticity of the implant is much greater than the modulus of elasticity of the native surrounding bone, the implant will take over the load bearing and the surrounding bone will start to decay. This will result in loosening of the implant and eventually ends in failure, the consequence of which is a revision surgery to replace the implant.

The present invention addresses the problem by providing kits of implants that contain varying ranges of modulus of elasticity. The implants used with the bone growth stimulation systems described herein can be packaged so that each kit or package includes a series of implants that each has a different modulus of elasticity. Thus, the kit includes implants of varying modulus of elasticity. The healthcare provider can determine the bone quality of each patient by performing a bone density scan at the implantation site and can then match an implant that has the nearest modulus of elasticity to the native bone at the implant site. In this way, the implant can be customized to match the bone density at the implant site of each patient, thus reducing the risk of reversion surgery.

For example, in one embodiment a kit can include the following implants, tools and materials: (1) a PISP 100 having a modulus of elasticity of between about 5 GPa and about 15 GPa (e.g., about 10 GPa in one embodiment); (2) a PISP 100 having a modulus of elasticity of between about 15 GPa and about 25 GPa (e.g., about 20 GPa in one embodiment); and (3) a PISP 100 having a modulus of elasticity of between about 25 GPa and about 35 GPa (e.g. about 30 GPa in one embodiment). In one embodiment, the kit can also include (1) a PISP 100 having a modulus of elasticity of between about 35 GPa and about 45 GPa (e.g., about 40 GPa in one embodiment); (2) an insertion/compression tool; (3) a removal/splaying tool; (4) synthetic or natural bone matrix, such as bone matrix pellets; (5) a wireless signal transmitter; and (6) instructions for use.

While the invention is susceptible to various modifications and alternative forms, specific examples thereof have been shown by way of example in the drawings and are herein described in detail. It should be understood, however, that the invention is not to be limited to the particular forms or methods disclosed, but to the contrary, the invention is to cover all modifications, equivalents, and alternatives falling within the spirit and scope of the appended claims.

We claim:

1. An interspinous fusion device comprising:
   a fixed anchor comprising a center ring, one or more fixed anchor arms projecting laterally from the center ring, and a barrel projecting transversely from the center ring;
   a polyaxial anchor comprising a socket ring and one or more polyaxial anchor arms projecting laterally from the socket ring, wherein the socket ring comprises a concave engagement surface; and
   a bone spacer comprising:
      a spacer head having a convex socket engagement surface that matches the concave engagement surface of the socket ring;
      one or more zip lock flanges extending transversely from the spacer head; and
      one or more bone abutments extending transversely from the spacer head,
   wherein the zip lock flanges and bone abutments of the bone spacer fit through the socket ring, the barrel of the fixed anchor fits through the socket ring, and the zip lock flanges engage with the barrel when the zip lock flanges and bone abutments are inserted through the socket ring, and
   wherein when the polyaxial anchor engages with the spacer head, the polyaxial anchor has a polyaxial freedom of movement relative to the spacer head as a result of a ball and socket engagement between the concave engagement surface of the socket ring and convex socket engagement surface of the spacer head.

2. The interspinous fusion device of claim 1, wherein each of said one or more zip lock flanges comprises a column of zip-locking teeth, and the barrel comprises one or more columns of zip-locking recesses shaped to receive the one or more zip-locking teeth in a locking engagement when the teeth are mated with the recesses.

3. The interspinous fusion device of claim 2, wherein the fixed anchor is reversibly locked to the bone spacer when the column of zip-locking teeth of the bone spacer engages the column of zip-locking recesses of the barrel of the fixed anchor.

4. The interspinous fusion device of claim 3, wherein once engaged, the bone spacer cannot be disengaged from the fixed anchor without a release tool that splays one or more of the flanges radially apart from the barrel.

5. The interspinous fusion device of claim 3, wherein once the fixed anchor and bone spacer are engaged with one another they cannot be disengaged without a splaying tool.

6. The interspinous fusion device of claim 1, wherein once the bone spacer is engaged with the fixed anchor they become radially fixed relative to one another and cannot rotate relative to one another.

7. The interspinous fusion device of claim 6, wherein the polyaxial anchor can radially rotate about the barrel, the one or more flanges and the one or more abutments.

* * * * *